United States Patent
Dohil et al.

(10) Patent No.: US 10,485,774 B2
(45) Date of Patent: *Nov. 26, 2019

(54) ENTERICALLY COATED CYSTEAMINE, CYSTAMINE AND DERIVATIVES THEREOF

(71) Applicant: The Regents of the University of California, Oakland, CA (US)

(72) Inventors: Ranjan Dohil, San Diego, CA (US); Jerry Schneider, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/922,520

(22) Filed: Mar. 15, 2018

(65) Prior Publication Data

US 2019/0060264 A1    Feb. 28, 2019

Related U.S. Application Data

(60) Continuation of application No. 15/656,903, filed on Jul. 21, 2017, now Pat. No. 9,925,158, which is a continuation of application No. 15/336,405, filed on Oct. 27, 2016, now Pat. No. 9,814,689, which is a continuation of application No. 14/950,234, filed on Nov. 24, 2015, now Pat. No. 9,511,039, which is a continuation of application No. 14/752,383, filed on Jun. 26, 2015, now Pat. No. 9,198,882, which is a division of application No. 14/555,993, filed on Nov. 28, 2014, now abandoned, which is a continuation of application No. 13/399,900, filed on Feb. 17, 2012, now abandoned, which is a continuation of application No. 13/190,396, filed on Jul. 25, 2011, now Pat. No. 8,129,433, which is a division of application No. 11/990,869, filed as application No. PCT/US2007/002325 on Jan. 26, 2007, now Pat. No. 8,026,284.

(60) Provisional application No. 60/762,715, filed on Jan. 27, 2006.

(51) Int. Cl.
| | |
|---|---|
| *A61K 31/194* | (2006.01) |
| *A61K 9/28* | (2006.01) |
| *A61K 31/13* | (2006.01) |
| *A61K 31/145* | (2006.01) |
| *A61K 9/00* | (2006.01) |
| *A61K 9/48* | (2006.01) |
| *A61K 9/50* | (2006.01) |
| *A61K 9/16* | (2006.01) |

(52) U.S. Cl.
CPC .......... *A61K 31/194* (2013.01); *A61K 9/0053* (2013.01); *A61K 9/1605* (2013.01); *A61K 9/284* (2013.01); *A61K 9/288* (2013.01); *A61K 9/2846* (2013.01); *A61K 9/2866* (2013.01); *A61K 9/2873* (2013.01); *A61K 9/4808* (2013.01); *A61K 9/5005* (2013.01); *A61K 9/5026* (2013.01); *A61K 9/5042* (2013.01); *A61K 9/5047* (2013.01); *A61K 9/5057* (2013.01); *A61K 9/5063* (2013.01); *A61K 31/13* (2013.01); *A61K 31/145* (2013.01)

(58) Field of Classification Search
CPC .. A61K 31/194; A61K 9/1605; A61K 9/5063; A61K 9/5026; A61K 9/2873; A61K 9/288; A61K 9/5042; A61K 9/5047; A61K 9/5057; A61K 9/5005; A61K 9/4808; A61K 9/0053; A61K 31/145; A61K 9/284
See application file for complete search history.

(56) References Cited

U.S. PATENT DOCUMENTS

| | | | |
|---|---|---|---|
| 2,809,918 | A | 10/1957 | Hermelin |
| 3,835,221 | A | 9/1974 | Fulberth et al. |
| 4,324,743 | A | 4/1982 | Feuer |
| 4,432,966 | A | 2/1984 | Zeitoun et al. |
| 4,728,512 | A | 3/1988 | Mehta et al. |
| 4,794,001 | A | 12/1988 | Mehta et al. |
| 4,959,306 | A | 9/1990 | Kameda |
| 5,225,202 | A | 7/1993 | Hodges et al. |
| 5,639,743 | A | 6/1997 | Kaswan et al. |
| 5,668,117 | A | 9/1997 | Shapiro |
| 6,331,316 | B1 | 12/2001 | Ullah et al. |
| 6,794,414 | B1 | 9/2004 | Steinman |
| 7,442,720 | B2 | 10/2008 | Chan et al. |
| 7,449,451 | B2 | 11/2008 | Prasad et al. |
| 7,759,398 | B2 | 7/2010 | Chan et al. |
| 7,893,113 | B2 | 2/2011 | Chan et al. |
| 8,026,284 | B2 | 9/2011 | Dohil et al. |
| 8,129,433 | B2 | 3/2012 | Dohil et al. |
| 8,188,151 | B2 | 5/2012 | Chan et al. |

(Continued)

FOREIGN PATENT DOCUMENTS

| | | |
|---|---|---|
| WO | 02/48110 A2 | 6/2002 |
| WO | 03/009699 A2 | 2/2003 |

(Continued)

OTHER PUBLICATIONS

US 9,238,198 B2, 01/2016, Makabe et al. (withdrawn)

(Continued)

*Primary Examiner* — Hasan S Ahmed
(74) *Attorney, Agent, or Firm* — Gavrilovich, Dodd & Lindsey LLP

(57) ABSTRACT

The disclosure provides oral cysteamine and cystamine formulations useful for treating cystinosis and neurodegenerative diseases and disorders. The formulations provide controlled release compositions that improve quality of life and reduced side-effects.

10 Claims, 4 Drawing Sheets

(56) References Cited

U.S. PATENT DOCUMENTS

| | | | |
|---|---|---|---|
| 8,415,398 B2 | 4/2013 | Liang et al. | |
| 9,192,590 B2* | 11/2015 | Dohil | A61K 9/284 |
| 9,198,882 B2* | 12/2015 | Dohil | A61K 9/284 |
| 9,511,039 B2 | 12/2016 | Dohil et al. | |
| 9,795,578 B2* | 10/2017 | Dohil | A61K 9/284 |
| 9,814,689 B2* | 11/2017 | Dohil | A61K 9/284 |
| 9,925,156 B2* | 3/2018 | Dohil | A61K 9/284 |
| 9,925,157 B2* | 3/2018 | Dohil | A61K 9/284 |
| 9,925,158 B2* | 3/2018 | Dohil | A61K 9/284 |
| 2001/0005716 A1 | 6/2001 | Ullah et al. | |
| 2003/0162747 A1 | 1/2003 | Kil | |
| 2003/0137125 A1 | 7/2003 | Booysen et al. | |
| 2003/0157191 A1 | 9/2003 | Kil | |
| 2004/0033985 A1 | 2/2004 | Chi | |
| 2004/0106591 A1 | 6/2004 | Pacioretty | |
| 2005/0004075 A1 | 1/2005 | Chi et al. | |
| 2005/0008702 A1 | 1/2005 | Faour et al. | |
| 2005/0027015 A1 | 2/2005 | Chi et al. | |
| 2005/0051103 A1 | 3/2005 | Chi et al. | |
| 2005/0089549 A1 | 4/2005 | Chi et al. | |
| 2005/0137125 A1 | 6/2005 | Chan et al. | |
| 2005/0209441 A1 | 9/2005 | Lile | |
| 2005/0245433 A1 | 11/2005 | Chan | |
| 2006/0140906 A1 | 6/2006 | Chan | |
| 2007/0078113 A1 | 4/2007 | Roth | |
| 2007/0172514 A1 | 7/2007 | Chi | |
| 2008/0276877 A1 | 11/2008 | Chi et al. | |
| 2009/0023632 A1 | 1/2009 | Adamson et al. | |
| 2009/0076166 A1 | 3/2009 | Dohil et al. | |
| 2009/0258030 A1 | 10/2009 | Chi et al. | |
| 2010/0303870 A1 | 12/2010 | Dohil et al. | |
| 2012/0237599 A1 | 9/2012 | Dohil et al. | |

FOREIGN PATENT DOCUMENTS

| | | |
|---|---|---|
| WO | 03/024438 A1 | 3/2003 |
| WO | 2003/070020 A1 | 8/2003 |
| WO | 2005/049002 A1 | 6/2005 |
| WO | 2005/063226 A1 | 7/2005 |
| WO | 2005/107730 A1 | 11/2005 |
| WO | 2007/082768 A1 | 7/2007 |
| WO | 2009/070781 A1 | 4/2009 |
| WO | 2009/100950 A1 | 10/2009 |

OTHER PUBLICATIONS

Arns et al., "Enteric coated mycophenlate sodium delivers bioequivalent MPA exposure compared with mycophenlate mofetil," 2005, pp. 199-206, vol. 19.

Ahmed, Hasan Syed, Office Action, U.S. Patent Publication No. 20100303870, United States Patent & Trademark Office, dated Mar. 2, 2011.

Ahmed, Hasan Syed, Office Action, U.S. Patent Publication No. 20090076166A1, United States Patent & Trademark Office, dated Feb. 1, 2011.

Ahmed, Hasan Syed, Notice of Allowance, U.S. Patent Publication No. 20090076166A1, United States Patent & Trademark Office, dated May 16, 2011.

Ahmed, Hasan Syed, Notice of Allowance, U.S. Patent Publication No. 20120237599A1, United States Patent & Trademark Office, dated Mar. 4, 2013.

Ahmed, Hasan Syed, Office Action, U.S. Patent Publication No. 20120237599A1, United States Patent & Trademark Office, dated Nov. 6, 2012.

Ahmed, Hasan Syed, Office Action, U.S. Patent Publication No. 20120237599A1, United States Patent & Trademark Office, dated Sep. 18, 2013.

Ahmed, Hasan Syed, Office Action, U.S. Patent Publication No. 20120237599A1, United States Patent & Trademark Office, dated Jun. 2, 2014.

Bacq et al., "The action of cysteamine on liver glycogen," Arch. Intern. de Physiologie, 1953, pp. 417-418, vol. LXI, No. 3.

Belldina et al., "Steady-state pharmacokinetics and pharmacodynamics of cysteamine bitartrate in paediatric nephropathic cystinosis patients," Br. J. Clin. Pharmacol., 2003, pp. 520-525, vol. 56.

Bendel-Stenzel et al., "Intravenous delivery of cysteamine for the treatment of cystinosis: association with hepatotoxicity," Pediatr Nephrol. Feb. 2008;23(2):311-5. Epub Aug. 1, 2007.

Brok et al., "Intervensions for paracetamol (adetominophen) overdose (Review)," The Cochrane Collaboration, 2009, Issue 1.

Butler et al., "Pantethine and Cystamien Depelete Cystine from Cystinotic Fribroblasts via Efflux of Cysteamine-Cysteine Mixed Disulfide," J. of Clin. Invest., Aug. 1984, pp. 411-416, vol. 74.

Castro et al., "Prevention by cystamine of liver necrosis and early biochemical alterations in dicued by carbon tetrachloride," Biochemical Pharmoacology, Jan. 1, 1972, pp. 49-52, vol. 21, No. 1.

Cystagon—Cysteamine bitartrate, Product Information, Alphapharm, 2008.

Cystagon Summary of Product Characteristics, first approved in 1997 and last updated in 2009.

Cystagon European public assessment report (EPAR), 2004.

Dohil et al., "Enteric-coated cysteamine for the treatment of paediatric non-alcoholic fatty liver disease," Aliment Pharmacol Ther. May 2011;33(9):1036-44. doi: 10.1111/j.1365-2036.2011.04626.x. Epub Mar. 13, 2011.

Dohil et al., "Long-term treatment of cystinosis in children with twice-daily cysteamine," J Pediatr. May 2010;156(5):823-7. Epub Feb. 6, 2010.

Dohil et al., "Twice-daily cysteamine bitartrate therapy for children with cystinosis," J Pediatr. Jan. 2010;156(1):71-75. e1-3. Epub.

Dohil et al., "Understanding intestinal cysteamine bitartrate absorption," J Pediatr. Jun. 2006;148(6):764-9.

Dohil et al., "Esomeprazole therapy for gastric acid hypersecretion in children with cystinosis," Pediatr Nephrol. Dec. 2005;20(12):1786-93. Epub Aug. 24, 2005.

Dohil et al., "The evaluation and treatment of gastrointestinal disease in children with cystinosis receiving cysteamine," J Pediatr. Aug. 2003;143(2):224-30.

Dohil et al., "Pharmacokinetics of cysteamine bitartrate following intraduodenal delivery," Fundam. Clin. Pharmacol., epub Oct. 31, 2012, pp. 136-143, vol. 28, No. 2.

Dohil et al., "The Effect of Food on Cysteamine Bitartrate Absorption in Healthy Participants," Clin. Pharmacol. in Drug Dev., Oct. 2012 (epub Jan. 10, 2013), pp. 170-174, vol. 1, No. 4.

Fidler et al., "Pharmacokinetics of cysteamine bitartrate following gastrointestinal infusion," Br J Clin Pharmacol. Jan. 2007;63(1):36-40.

Fischer, P., "Hepatic glycogen, x-rays, and cysteamine," 1954, pp. 134-136.

Gangoiti et al., "Pharmacokinetics of enteric-coated cysteamine bitartrate in healthy adults: a pilot study," Br J Clin Pharmacol. Sep. 2010;70(3):376-82.

Kleta et al., "Pharmacological treatmetn of nephropathic cystinosis with cysteamine," Expert Opin. Pharmacother., 2004, pp. 2255-2262, vol. 5, No. 11.

Kleta, Robert, "A Deeper Look Into Cysteamine Abbsorption for the Treatment of Cystinosis," J of Pediatrics, 2006, pp. 718-719, vol. 148, No. 6.

Langman et al., "A Randomized Controlled Crossover Trial with Delayed-Release Cysteamine Bitartrate in Nephropathic Cystinosis: Effectiveness on White Blood Cell Cystine Levels and Comparison of Safety," Clin. J. Am. Soc. Nephrol., Jul. 2012, pp. 1112-1120, vol. 7.

Langman et al., "Quality of Life is Improved and Kidney Function Preserved in Patients with Nephropathic Cystinosis Treated for 2 Years with Delayed-Release Cysteamine Bitartrate," J. Pediatr., Sep. 2014, pp. 528-533, vol. 165, No. 3.

Levtchenko et al., "Strict cysteamine dose regimen is required to prevent nocturnal cystine accumulation in cystinosis," Pediatric Nephrol., 2006, pp. 110-113, vol. 21.

Manowska et al., "Liver and Muscle Glycogen Contents and Blood Glucose Concentration after AET or MEA Treatment of Adult Male Mice," Folia Biologica, 1991, pp. 29-31, vol. 31, No. 1-4.

(56) References Cited

OTHER PUBLICATIONS

Miners et al., "Mechanism of action of paracetomol protective agents in mice in vivo," Biochemical Pharmacology, 1984, pp. 2995-3000, vol. 33, No. 19.
"Natalie's Wish", Fall 2004.
"Natalie's Wish", Cystinosis Research Foundation, Spring 2005.
"Natalie's Wish", Cystinosis Research Foundation, Spring 2004.
Owen et al., "Pilot Scale Manufacture of Gastro-Resistant Cysteamine Hydrochloride Pellets Using Extrusion Spheronization and Fluid Bed Coating," 15th Pharm. Tech. Conf., 1996, pp. 116-119, vol. 1.
Owen et al., "Development of Cysteamine Hydrochloride Pellets for Cystinotic Infants," Eu. Hosp. Pharm., 1997, pp. 136-142, vol. 3, No. 4.
Owen et al., "The effect of Colloidal Grade of Microcrystalline Cellulose on the Extrusion Rheology and Spheronisation of Cysteamine Hydrochloride Formulations," 16th Pharm. Tech. Conf., 1997.
Owen, Berwyn, "Formulation and Processing of Cysteamine Hydrochloride Gastro-Resistant Pellets for the Treatmeni of Cystinosis," Thesis, Institute of Pharm. and Chem. School of Sciences, University of Sunderland, Feb. 2000.
Owen et al., "Film Coating of Cysteamine Hydrochloride Pellets for the Treatment of Cystinosis in Children," Pharm. Tech. Conf., 2001, pp. 139-140, Issue 20.
Paoletti et al, "A new hepatic- and irradiation-protective agent, 2-methylpiperazine Dithioformate," 1960, pp. 688-696.
Powell et al., "An unexpected problem in the clinical assessment of cystinosis," Pediatr. Nephrol., 2012, pp. 687-688, vol. 27.
PROCYSBI(TM)—(Cysteamine bitartrate) delayed-release capsules, 2013.
Schneider, Jerry A., "Cystinosis: crystals to genes," Pediatr. Nephrol., 2008, pp. 1910, vol. 23.
Schneider et al., "Recent advances in the treatment of cystinosis," J. Inher. Metab. Dis., 1995, pp. 387-397, vol. 18.
Shiratori et al., "Evidence for Significant Role of Gastrin in Cysteamine-Induced Hypersecretion of Gastric Acid," J. of Clin. Gastroenterol., 1997, pp. S84-S88, vol. 25.
Smolin et al., "A Comparison of the Effectiveness of Cysteamine and Phosphocysteamine in Elevating Plasma Cysteamine Concentration and Decreasing Leukocyte Free Cystine in Nephropathic Cystinosis," Ped. Research, 1988, pp. 616-620, vol. 23, No. 6.
Sokal et al., "Glycogenolytic action of mercaptoethylamine," Am. J. Physiol., 1959, pp. 261-264, vol. 196, No. 2.
Tenneze et al., "A study of the relative bioavailability of cysteamine hydrochloride, cysteamine bitartrate and phosphocysteamine in healthy adult make volunteers," Br. J. Clin. Pharmacol., 47:49-52, 1999.
Thoene et al., "Cystinosis intracellular cystine depletion by aminothiols in vitro and in vivo," J. Clinical Investigation, Jul. 1976, pp. 180-189, vol. 58.
Van de Berg et al., "Contribution of Gastrin to Cysteamine-induced Gastric Acid Secretion in Rats," Life Sciences, 1993, pp. 1861-1867, vol. 52, No. 23.
Van Cauwenberge et al, "Carbohydrate metabolism, adrenal cortex, and sulfur radio-protectors," 1954, pp. 645-649.
Van Stralen et al., "Improvement in the Renal Prognosis in Nephropathic Cystinosis," Clin. J. of the Amer. Soc. of Nephrol., Oct. 2011, pp. 2485-2491, vol. 6.
Wang et al., "Cerebral PET imaging and histological evidence of transglutaminase inhibitor cysteamine induced neuroprotection in transgenic R6/2 mouse model of Huntington's disease," J. of the Neurological Sciences, Apr. 2005, pp. 57-66, vol. 231.
Young, Lee W., International Search Report and Written Opinion, PCT/US08/85064, dated Feb. 13, 2009.
Goodhart et al., "An evaluation of aqueous film-forming dispersions for controlled release," Pharm. Tech., 8 (4):64-71, 1984.
Markello et al., "Improved Renal Function in Children with Cystinosis Treated with Cysteamine", Apr. 22, 1993, vol. 328, No. 16, pp. 1157-1162.
Emma et al., "Nephropathic cystinosis: an international consensus document", Nephrol Dial Transplant, 2014, 29: iv87-iv94.
Horizon Pharma plc Announces Health Canada Approval of PROCYSBI™ (Cysteamine Delayed-Release Capsules) for the Treatment of Nephropathic Cystinosis, Press Release, Jun. 19, 2017.
Horizon Pharma plc Announces Four Poster Presentations on PROCYSBI® (Cysteamine Bitartrate) Delayed-Release Capsules at Cystinosis Research Network 2017 Family Conference, Press Release, Jul. 14, 2017.
Horizon Pharma plc Announces Availability of PROCYSBI™ (cysteamine bitartrate) in Canada, Press Release, Oct. 26, 2017.

\* cited by examiner

ENTERICALLY COATED CYSTEAMINE, CYSTAMINE AND DERIVATIVES THEREOF

CROSS-REFERENCE TO RELATED APPLICATIONS

This application is a continuation of U.S. application Ser. No. 15/656,903, filed Jul. 21, 2017, which is a continuation of U.S. application Ser. No. 15/336,405, filed Oct. 27, 2016 (now U.S. Pat. No. 9,814,689), which is a continuation of U.S. application Ser. No. 14/950,234, filed Nov. 24, 2015 (Now U.S. Pat. No. 9,511,039), which is a continuation of U.S. application Ser. No. 14/752,383, filed Jun. 26, 2015 (now U.S. Pat. No. 9,198,882), which is a divisional of U.S. application Ser. No. 14/555,993, filed Nov. 28, 2014, which is a continuation of U.S. application Ser. No. 13/399,900, filed Feb. 17, 2012, which is a continuation of U.S. application Ser. No. 13/190,396, filed Jul. 25, 2011 (now U.S. Pat. No. 8,129,433), which is a divisional of U.S. application Ser. No. 11/990,869, filed Nov. 13, 2008 (now U.S. Pat. No. 8,026,284), which is a U.S. National Stage Application filed under 35 U.S.C. § 371 and claims priority to International Application No. PCT/US07/02325, filed Jan. 26, 2007, which application claims priority under 35 U.S.C. § 119 to U.S. Provisional Application Ser. No. 60/762,715, filed Jan. 27, 2006, the disclosures of which are incorporated herein by reference.

FIELD OF THE INVENTION

The invention relates to methods, compositions and treatments for metabolic conditions and free radical damage. More specifically, the invention relates to methods and composition useful for treating Cystinosis and neurodegenerative diseases such as Huntington's, Alzheimer's and Parkinson's disease, as free radical and radioprotectants, and as hepto-protectant agents.

BACKGROUND

Cystinosis is a rare, autosomal recessive disease caused by intra-lysosomal accumulation of the amino acid cystine within various tissues, including the spleen, liver, lymph nodes, kidney, bone marrow, and eyes. Nephropathic cystinosis is associated with kidney failure that necessitates kidney transplantation. To date, the only specific treatment for nephropathic cystinosis is the sulfhydryl agent, cysteamine. Cysteamine has been shown to lower intracellular cystine levels, thereby reducing the rate of progression of kidney failure in children.

Cysteamine, through a mechanism of increased gastrin and gastric acid production, is ulcerogenic. When administered orally to children with cystinosis, cysteamine has also been shown to cause a 3-fold increase in gastric acid production and a 50% rise of serum gastrin levels. As a consequence, subjects that use cysteamine suffer gastrointestinal (GI) symptoms and are often unable to take cysteamine regularly or at full dose.

To achieve sustained reduction of leukocyte cystine levels, patients are normally required to take oral cysteamine every 6 hours, which invariably means having to awaken from sleep. However, when a single dose of cysteamine was administered intravenously the leukocyte cystine level remained suppressed for more than 24 hours, possibly because plasma cysteamine concentrations were higher and achieved more rapidly than when the drug is administered orally. Regular intravenous administration of cysteamine would not be practical. Accordingly, there is a need for formulations and delivery methods that would result in higher plasma, and thus intracellular, concentration as well as decrease the number of daily doses and therefore improve the quality of life for patients.

SUMMARY

The invention provides a composition comprising an enterically coated cystamine or cystamine derivative.

The invention also provides a composition comprising an enterically coated cysteamine or cysteamine derivative.

The invention further provides a composition comprising a coated cystinosis therapeutic agent that has increased uptake in the small intestine compared to a non-coated cystinosis therapeutic agent when administered orally. In one aspect, the coated cystinosis therapeutic agent comprises a cysteamine or cysteamine derivative.

The invention also provides a method of treating a subject with cystinosis, comprising administering to the subject a composition of the invention.

The invention also contemplates a method of treating a subject with a neurodegenerative disease or disorder comprising administering to the subject a composition of the invention comprising an enterically coated cystamine or cystamine derivative.

The invention provides a pharmaceutical formulation comprising a composition of the invention further including various pharmaceutically acceptable agents (e.g., flavorants, binders and the like) in a pharmaceutically acceptable carrier.

The invention provides a method of treating cystinosis or a neurodegenerative disease or disorder comprising administering a composition of the invention and a second therapeutic agent.

DETAILED DESCRIPTION

Figure 1A:
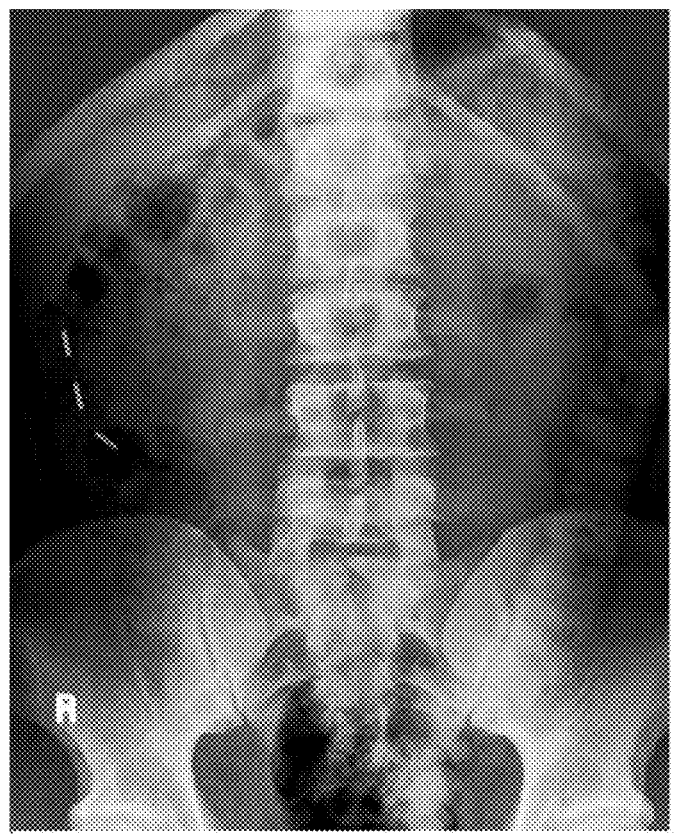
FIG. 1A-B shows enterocolonic tube. (A) Is an abdominal X-ray film showing the radiopaque weighted tip of the tube entering the ascending colon. (B) Is a contrast infused picture. The tube has passed through the small intestine and the tip is confirmed.

As used herein and in the appended claims, the singular forms "a," "an," and "the" include plural referents unless the context clearly dictates otherwise. Thus, for example, reference to "a derivative" includes a plurality of such derivatives and reference to "a subject" includes reference to one or more subjects known to those skilled in the art, and so forth.

Unless defined otherwise, all technical and scientific terms used herein have the same meaning as commonly understood to one of ordinary skill in the art to which this disclosure belongs. Although methods and materials similar or equivalent to those described herein can be used in the practice of the disclosed methods and compositions, the exemplary methods, devices and materials are described herein.

The publications discussed above and throughout the text are provided solely for their disclosure prior to the filing date of the present application. Nothing herein is to be construed as an admission that the inventors are not entitled to antedate such disclosure by virtue of prior disclosure.

Cystinosis is a metabolic disease characterized by an abnormal accumulation of the amino acid cystine in various organs of the body such as the kidney, eye, muscle, pancreas, and brain. Different organs are affected at different ages.

There are three clinical forms of cystinosis. Infantile (or nephropathic) cystinosis; late-onset cystinosis; and benign cystinosis. The latter form does not produce kidney damage. Infantile cystinosis is usually diagnosed between 6 and 18 months of age with symptoms of excessive thirst and urination, failure to thrive, rickets, and episodes of dehydration. These findings are caused by a disorder called renal tubulopathy or Fanconi syndrome. As a consequence important nutrients and minerals are lost in the urine. Children with cystinosis also have crystals in their eyes (after one year of age) which may lead to photosensitivity. They also have an increased level of cystine in their white blood cells without adverse effect but allowing the diagnosis to be ascertained. Without specific treatment, children with cystinosis develop end-stage renal failure, i.e., lose their kidney function, usually between 6 and 12 years of age. Without cysteamine treatment subjects can develop complications in other organs due to the continued accumulation of cystine throughout the body. These complications can include muscle wasting, difficulty swallowing, diabetes, and hypothyroidism.

Some symptoms include the inability of the kidneys to concentrate urine and allow important quantities of sodium, potassium, phosphorus, bicarbonate and substances like carnitine to be excreted in the urine. Treatment of symptoms compensates for these urinary losses. Subjects need to drink large quantities of water, because up to 2 to 3 liters of water are lost in the urine every day driving the feeling of being thirsty. In addition, the loss of urinary electrolytes (sodium, potassium, bicarbonate, phosphorus) must be compensated in the subject. It is often necessary to add a salt supplement in the form of sodium chloride. Children also lose bicarbonate and potassium in the urine, which can be compensated for by giving sodium bicarbonate and potassium bicarbonate.

Specific treatments of cystinosis aim to reduce cystine accumulation within the cells. Cystinosis is currently treated with cysteamine (Cystagon®). Cysteamine also improves growth of cystinosis children. Cysteamine is only active in a very short period of time not exceeding 5-6 hours, thus requiring administration of Cystagon® capsules 4 times a day, that is to say about every 6 hours. This treatment is also only effective if continued day after day, indefinitely in order to control the disease. About 1000 children require lifelong treatment to prolong their lives and prevent deterioration of kidney function. However, as mentioned above, cysteamine administration results in increased gastric secretions and is ulcerogenic. In addition, routes and timing of administration provide difficulty for subjects in need of such therapy. Recently, a similar drug called cystamine (the disulfide form of cysteamine) has been studied for neurodegenerative disorders including Huntington's and Parkinson's diseases. Cystamine has similar side-effects and dosing difficulties to that of cysteamine.

Cysteamine is a potent gastric acid-secretagogue that has been used in laboratory animals to induce duodenal ulceration; studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2- to 3-fold rise in gastric acid-hypersecretion. Symptoms suffered by these individuals included abdominal pain, heartburn, nausea, vomiting, and anorexia. The disclosure demonstrates that cysteamine-induced hypergastrinemia arises, in part, as a local effect on the gastric antral-predominant G-cells in susceptible individuals. The data also suggest that this is also a systemic effect of gastrin release by cysteamine. Depending upon the route of administration, plasma gastrin levels usually peak after intragastric delivery within 30 minutes, whereas the plasma cysteamine levels peak later.

Subjects with cystinosis are required to ingest oral cysteamine (Cystagon®) every 6 hours, day and night. When taken regularly, cysteamine can deplete intracellular cystine by up to 90% (as measured in circulating white blood cells), and this has been shown to reduce the rate of progression to kidney failure/transplantation and also to obviate the need for thyroid replacement therapy. Unfortunately, because of the strict treatment regimen and the associated symptoms, non-adherence with cysteamine therapy remains a problem, particularly among adolescent and young adult patients. By reducing the frequency of required cysteamine dosing, adherence to a therapeutic regimen can be improved. The disclosure demonstrates that delivery of cysteamine to the small intestine reduces gastric distress and ulceration and improves bioavailability of cysteamine in the circulation. Delivery of cysteamine into the small intestine is useful due to improved absorption rate from the SI, greater surface area of the SI, and/or less cysteamine undergoing hepatic first pass elimination when absorbed through the small intestine. This disclosure shows a dramatic decrease in leukocyte cystine within an hour of cysteamine delivery.

In addition, sulfhydryl (SH) compounds such as cysteamine, cystamine, and glutathione are among the most important and active intracellular antioxidants. Cysteamine protects animals against bone marrow and gastrointestinal radiation syndromes. The rationale for the importance of SH compounds is further supported by observations in mitotic cells. These are the most sensitive to radiation injury in terms of cell reproductive death and are noted to have the lowest level of SH compounds. Conversely, S-phase cells, which are the most resistant to radiation injury using the same criteria, have demonstrated the highest levels of inherent SH compounds. In addition, when mitotic cells were treated with cysteamine, they became very resistant to radiation. It has also been noted that cysteamine may directly protect cells against induced mutations. The protection is thought to result from scavenging of free radicals, either directly or via release of protein-bound GSH. An enzyme that liberates cysteamine from coenzyme A has been reported in avian liver and hog kidney. Recently, studies have appeared demonstrating a protective effect of cysteamine against the hepatotoxic agents: acetaminophen, bromobenzene, and phalloidin.

Cystamine, in addition, to its role as a radioprotectant, has been found to alleviate tremors and prolong life in mice with the gene mutation for Huntington's disease (HD). The drug may work by increasing the activity of proteins that protect nerve cells, or neurons, from degeneration. Cystamine appears to inactivate an enzyme called transglutaminase and thus results in a reduction of huntingtin protein (Nature Medicine 8, 143-149, 2002). In addition, cystamine was found to increase the levels of certain neuroprotective proteins. However, due to the current methods and formulation of delivery of cystamine, degradation and poor uptake require excessive dosing.

The disclosure is not limited with respect to a specific cysteamine or cystamine salt or ester or derivative; the compositions of the disclosure can contain any cysteamine or cystamine, cysteamine or cystamine derivative, or combination of cysteamine or cystamines. The active agents in the composition, i.e., cysteamine or cystamine, may be administered in the form of a pharmacologically acceptable salt, ester, amide, prodrug or analog or as a combination thereof. Salts, esters, amides, prodrugs and analogs of the active agents may be prepared using standard procedures known to those skilled in the art of synthetic organic chemistry and described, for example, by J. March, "Advanced Organic Chemistry: Reactions, Mechanisms and Structure," 4th Ed. (New York: Wiley-Interscience, 1992). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula R—COOH where R is alkyl, and typically is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

The disclosure provides delivery methods and compositions that overcome the problems associated with cysteamine and cystamine delivery. The methods of compositions of the disclosure provide enteric-coated compositions that result in less frequent dosing (2x/day vs. 4x/day), increased patient compliance and fewer gastrointestinal side effects (e.g., pain, heartburn, acid production, vomiting) and other side effects (e.g., patients smell like rotten eggs—a particular compliance problem as subjects reach puberty). The disclosure provides enteric-coated cysteamine compositions (sulfhydryl/Cystagon®) and cystamine compositions.

The disclosure provides methods for the treatment of cystinosis, the treatment of neurodegenerative disease such as Alzheimer Disease, Huntington's and Parkinson's disease and free radical damage using enterically coated cysteamine and cystamine, respectively.

The disclosure provides composition comprising enterically formulated cysteamine and cystamine derivatives. Examples of cysteamine derivatives include hydrochloride, bitartrate and phosphocysteamine derivatives. Cystamine and cystamine derivatives include sulfated cystamine. Enteric coatings prolong release until the cystamine, cystamine derivative, or cysteamine derivative/Cystagon® reaches the intestinal tract, typically the small intestine. Because of the enteric coatings, delivery to the small intestine is improved thereby improving uptake of active ingredient while reducing gastric side effects. This will result in a reduction in the need for frequent administration that currently is associated with Cystagon® therapy, cysteamine and cystamine therapy.

An "enterically coated" drug or tablet refers to a drug or tablet that is coated with a substance—i.e., with an "enteric coating"—that remains intact in the stomach but dissolves and releases the drug once the small intestine is reached.

As used herein "enteric coating", is a material, a polymer material or materials which encase the medicament core (e.g., cystamine, cysteamine, Cystagon®). Typically, a substantial amount or all of the enteric coating material is dissolved before the medicament or therapeutically active agent is released from the dosage form, so as to achieve delayed dissolution of the medicament core. A suitable pH-sensitive polymer is one which will dissolve in intestinal juices at a higher pH level (pH greater than 4.5), such as within the small intestine and therefore permit release of the pharmacologically active substance in the regions of the small intestine and not in the upper portion of the GI tract, such as the stomach.

The coating material is selected such that the therapeutically active agent will be released when the dosage form reaches the small intestine or a region in which the pH is greater than pH 4.5. The coating may be a pH-sensitive materials, which remain intact in the lower pH environs of the stomach, but which disintegrate or dissolve at the pH commonly found in the small intestine of the patient. For example, the enteric coating material begins to dissolve in an aqueous solution at pH between about 4.5 to about 5.5. For example, pH-sensitive materials will not undergo significant dissolution until the dosage form has emptied from the stomach. The pH of the small intestine gradually increases from about 4.5 to about 6.5 in the duodenal bulb to about 7.2 in the distal portions of the small intestine (ileum). In order to provide predictable dissolution corresponding to the small intestine transit time of about 3 hours (e.g., 2-3 hours) and permit reproducible release therein, the coating should begin to dissolve within the pH range of the duodenum, and continue to dissolve at the pH range within the small intestine. Therefore, the amount of enteric polymer coating should be sufficient to substantially dissolve during the approximate three hour transit time within the small intestine (e.g., the proximal and mid-small intestine).

Enteric coatings have been used for many years to arrest the release of the drug from orally ingestible dosage forms. Depending upon the composition and/or thickness, the enteric coatings are resistant to stomach acid for required periods of time before they begin to disintegrate and permit release of the drug in the lower stomach or upper part of the small intestines. Examples of some enteric coatings are disclosed in U.S. Pat. No. 5,225,202 which is incorporated by reference fully herein. As set forth in U.S. Pat. No. 5,225,202, some examples of coating previously employed are beeswax and glyceryl monostearate; beeswax, shellac and cellulose; and cetyl alcohol, mastic and shellac, as well as shellac and stearic acid (U.S. Pat. No. 2,809,918); polyvinyl acetate and ethyl cellulose (U.S. Pat. No. 3,835,221); and neutral copolymer of polymethacrylic acid esters (Eudragit L30D) (F. W. Goodhart et al., Pharm. Tech., pp. 64-71, April 1984); copolymers of methacrylic acid and methacrylic acid methylester (Eudragits), or a neutral copolymer of polymethacrylic acid esters containing metallic stearates (Mehta et al., U.S. Pat. Nos. 4,728,512 and 4,794,001). Such coatings comprise mixtures of fats and fatty acids, shellac and shellac derivatives and the cellulose acid phthlates, e.g., those having a free carboxyl content. See, Remington's at page 1590, and Zeitova et al. (U.S. Pat. No. 4,432,966), for descriptions of suitable enteric coating compositions. Accordingly, increased adsorption in the small intestine due to enteric coatings of cystamine, cysteamine derivatives (including Cystagon®) can result in improvements in cystinosis as well as neurodegenerative diseases including, for example, Huntington's disease.

Generally, the enteric coating comprises a polymeric material that prevents cysteamine or cystamine release in the low pH environment of the stomach but that ionizes at a slightly higher pH, typically a pH of 4 or 5, and thus dissolves sufficiently in the small intestines to gradually release the active agent therein. Accordingly, among the most effective enteric coating materials are polyacids having a $pK_a$ in the range of about 3 to 5. Suitable enteric coating materials include, but are not limited to, polymerized gelatin, shellac, methacrylic acid copolymer type C NF, cellulose butyrate phthalate, cellulose hydrogen phthalate, cellulose proprionate phthalate, polyvinyl acetate phthalate (PVAP), cellulose acetate phthalate (CAP), cellulose acetate trimellitate (CAT), hydroxypropyl methylcellulose phthalate, hydroxypropyl methylcellulose acetate, dioxypropyl methylcellulose succinate, carboxymethyl ethylcellulose (CMEC), hydroxypropyl methylcellulose acetate succinate (HPMCAS), and acrylic acid polymers and copolymers, typically formed from methyl acrylate, ethyl acrylate, methyl methacrylate and/or ethyl methacrylate with copolymers of acrylic and methacrylic acid esters (Eudragit NE, Eudragit RL, Eudragit RS). For example, the enterically coating can comprise Eudragit L30D, triethylcitrate, and hydroxypropylmethylcellulose (HPMC), Cystagon® (or other cysteamine derivative), wherein the coating comprises 10 to 13% of the final product.

By "pharmaceutically acceptable carrier" or "pharmaceutically acceptable vehicle" are meant materials that are suitable for oral administration and not biologically, or otherwise, undesirable, i.e., that may be administered to a subject along with an active ingredient without causing any undesirable biological effects or interacting in a deleterious manner with any of the other components of a pharmaceutical composition in which it is contained.

Similarly, a "pharmaceutically acceptable" salt, ester or other derivative of an active agent comprise, for example, salts, esters or other derivatives which are not biologically or otherwise undesirable.

"Stabilizing agents" refer to compounds that lower the rate at which pharmaceutical degrades, particularly an oral pharmaceutical formulation under environmental conditions of storage.

By the terms "effective amount" or "therapeutically effective amount" of a enteric formulation of cysteamine or cystamine refers to a nontoxic but sufficient amount of the agent to provide the desired therapeutic effect. As will be pointed out below, the exact amount required will vary from subject to subject, depending on the age, weight, and general condition of the subject, the severity of the condition being treated, and the like. An appropriate "effective" amount in any individual case may be determined by one of ordinary skill in the art using only routine experimentation.

In one aspect of the disclosure there is provided a stabilized pharmaceutical composition for administration of an cysteamine or cystamine, wherein the cysteamine or cystamine is enterically coated.

The cysteamine or cystamine is present in the composition in a therapeutically effective amount; typically, the composition is in unit dosage form. The amount of cysteamine or cystamine administered will, of course, be dependent on the age, weight, and general condition of the subject, the severity of the condition being treated, and the judgment of the prescribing physician. Suitable therapeutic amounts will be known to those skilled in the art and/or are described in the pertinent reference texts and literature. In one aspect, the dose is administered twice per day at about 0.5-1.0 $g/m^2$ (e.g., 0.7-0.8 $g/m^2$) body surface area. Current non-enterically coated doses are about 1.35 $g/m^2$ body surface area and are administered 4-5 times per day.

The entericaly coated cysteamine or cystamine can comprise various excipients, as is well known in the pharmaceutical art, provided such excipients do not exhibit a destabilizing effect on any components in the composition. Thus, excipients such as binders, bulking agents, diluents, disintegrants, lubricants, fillers, carriers, and the like can be combined with the cysteamine or cystamine. For solid compositions, diluents are typically necessary to increase the bulk of a tablet so that a practical size is provided for compression. Suitable diluents include dicalcium phosphate, calcium sulfate, lactose, cellulose, kaolin, mannitol, sodium chloride, dry starch and powdered sugar. Binders are used to impart cohesive qualities to a tablet formulation, and thus ensure that a tablet remains intact after compression. Suitable binder materials include, but are not limited to, starch (including corn starch and pregelatinized starch), gelatin, sugars (including sucrose, glucose, dextrose and lactose), polyethylene glycol, waxes, and natural and synthetic gums, e.g., acacia sodium alginate, polyvinylpyrrolidone, cellulosic polymers (including hydroxypropyl cellulose, hydroxypropyl methylcellulose, methyl cellulose, hydroxyethyl cellulose, and the like), and Veegum. Lubricants are used to facilitate tablet manufacture; examples of suitable lubricants include, for example, magnesium stearate, calcium stearate, and stearic acid, and are typically present at no more than approximately 1 weight percent relative to tablet weight. Disintegrants are used to facilitate tablet disintegration or "breakup" after administration, and are generally starches, clays, celluloses, algins, gums or crosslinked polymers. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. If desired, flavoring, coloring and/or sweetening agents may be added as well. Other optional components for incorporation into an oral formulation herein include, but are not limited to, preservatives, suspending agents, thickening agents, and the like. Fillers include, for example, insoluble materials such as silicon dioxide, titanium oxide, alumina, talc, kaolin, powdered cellulose, microcrystalline cellulose, and the like, as well as soluble materials such as mannitol, urea, sucrose, lactose, dextrose, sodium chloride, sorbitol, and the like.

A pharmaceutical composition may also comprise a stabilizing agent such as hydroxypropyl methylcellulose or polyvinylpyrrolidone, as disclosed in U.S. Pat. No. 4,301,146. Other stabilizing agents include, but are not limited to, cellulosic polymers such as hydroxypropyl cellulose, hydroxyethyl cellulose, methyl cellulose, ethyl cellulose, cellulose acetate, cellulose acetate phthalate, cellulose acetate trimellitate, hydroxypropyl methylcellulose phthalate, microcrystalline cellulose and carboxymethylcellulose sodium; and vinyl polymers and copolymers such as polyvinyl acetate, polyvinylacetate phthalate, vinylacetate crotonic acid copolymer, and ethylene-vinyl acetate copolymers. The stabilizing agent is present in an amount effective to provide the desired stabilizing effect; generally, this means that the ratio of cysteamine or cystamine to the stabilizing agent is at least about 1:500 w/w, more commonly about 1:99 w/w.

The tablets are manufactured by first enterically coating the cysteamine or cystamine. A method for forming tablets herein is by direct compression of the powders containing the enterically coated cysteamine or cystamine, optionally in combination with diluents, binders, lubricants, disintegrants, colorants, stabilizers or the like. As an alternative to direct compression, compressed tablets can be prepared using wet-granulation or dry-granulation processes. Tablets may also be molded rather than compressed, starting with a moist material containing a suitable water-soluble lubricant.

In an alternative embodiment, the enterically coated cysteamine or cystamine are granulated and the granulation is compressed into a tablet or filled into a capsule. Capsule materials may be either hard or soft, and are typically sealed, such as with gelatin bands or the like. Tablets and capsules for oral use will generally include one or more commonly used excipients as discussed herein.

For administration of the dosage form, i.e., the tablet or capsule comprising the enterically coated cysteamine or cystamine, a total weight in the range of approximately 100 mg to 1000 mg is used. The dosage form is orally administered to a patient suffering from a condition for which an cysteamine or cystamine would typically be indicated, including, but not limited to, cystinosis and neurodegenerative diseases such as Huntington's, Alzheimer's and Parkinson's disease.

The compositions of the disclosure can be used in combination with other therapies useful for treating cystinosis and neurodegenerative diseases and disorders. For example, indomethacin therapy (Indocid® or Endol®) is an anti-inflammatory used to treat rheumatoid arthritis and lumbago, but it can be used to reduce water and electrolyte urine loss. In children with cystinosis, indomethacin reduces the urine volume and therefore liquid consumption by about 30%, sometimes by half. In most cases this is associated with an appetite improvement. Indomethacin treatment is generally followed for several years.

Other therapies can be combined with the methods and compositions of the disclosure to treat diseases and disorders that are attributed or result from cystinosis. Urinary phosphorus loss, for example, entails rickets, and it may be necessary to give a phosphorus supplement. Carnitine is lost in the urine and blood levels are low. Carnitine allows fat to be used by the muscles to provide energy. Hormone supplementation is sometimes necessary. Sometimes the thyroid gland will not produce enough thyroid hormones. This is given as thyroxin (drops or tablets). Insulin treatment is sometimes necessary if diabetes appears, when the pancreas does not produce enough insulin. These treatments have become rarely necessary in children whom are treated with cysteamine, since the treatment protects the thyroid and the pancreas. Some adolescent boys require a testosterone treatment if puberty is late. Growth hormone therapy may be indicated if growth is not sufficient despite a good hydro electrolytes balance. Accordingly, such therapies can be combined with the enterically coated cysteamine and cystamine compositions and methods of the disclosure.

The effectiveness of a method or composition of the disclosure can be assessed by measuring leukocyte cystine concentrations. Dosage adjustment and therapy can be made by a medical specialist depending upon, for example, the severity of cystenosis and/or the concentration of cystine. Additional therapies including the use of omeprazole (Prilosec®) can reduce these symptoms.

In addition, various prodrugs can be "activated" by use of the enterically coated cysteamine. Prodrugs are pharmacologically inert, they themselves do not work in the body, but once they have been absorbed, the prodrug decomposes. The prodrug approach has been used successfully in a number of therapeutic areas including antibiotics, antihistamines and ulcer treatments. The advantage of using prodrugs is that the active agent is chemically camouflaged and no active agent is released until the drug has passed out of the gut and into the cells of the body. For example, a number of produgs use S—S bonds. Weak reducing agents, such as cysteamine, reduce these bonds and release the drug. Accordingly, the compositions of the disclosure are useful in combination with pro-drugs for timed release of the drug. In this aspect, a pro-drug can be administered followed by administration of an enterically coated cysteamine compositions of the invention (at a desired time) to activate the pro-drug.

It is to be understood that while the invention has been described in conjunction with specific embodiments thereof, that the foregoing description as well as the examples which follow are intended to illustrate and not limit the scope of the invention. Other aspects, advantages and modifications within the scope of the invention will be apparent to those skilled in the art to which the invention

EXAMPLES

Subjects.

Children with cystinosis, ≥12 years old, and taking regular cysteamine bitartrate (Cystagon®; Mylan, Morgantown, W. Va.) were recruited to the study (Table I). Adult control patients were recruited locally. Patients with cystinosis had a mean leukocyte cystine level of less than 2.0 nmol half-cystine/mg protein over the past year. Cysteamine therapy was discontinued 2 days before admission, and acid suppressants, antibiotics, nonsteroidal anti-inflammatory drugs, pro-kinetic agents, and antihistamines were discontinued 2 weeks before admission. None of the patients had undergone kidney transplantation. Baseline chemistry, Helicobacter pylori serologic study, complete blood count, and urinalysis were performed.

TABLE I

Cystinosis patient data

| Patient | Age (yrs.) | Sex | Weight (kg) | Cysteamine dose (mg)* | Serum creatinine (mg/dL) |
|---|---|---|---|---|---|
| 1 | 16 | Male | 61.5 | 500 | 1.0 |
| 2 | 14 | Male | 39.4 | 406 | 1.2 |
| 3 | 13 | Female | 39.1 | 406 | 1.5 |
| 4 | 19 | Female | 38.1 | 406 | 1.4 |
| 5 | 13 | Female | 50.1 | 500 | 1.0 |
| 6 | 16 | Male | 58.7 | 500 | 3.1 |

*Dose of cysteamine base delivered into varying delivery sites

Cysteamine Bitartrate Delivery.

Cysteamine was infused through a silicone rubber nasoenteric tube (Dentsleeve Pty Ltd, Australia), 3 mm in diameter and 4.5 meters long. The tube, specifically made for this study, had a tungsten-weighted tip, and immediately proximal to this was an inflatable balloon (5-mL capacity). Immediately proximal to the balloon was an infusion port (1 mm diameter) through which the drug was delivered. After an overnight fast (except for water), the dose of cysteamine bitartrate (10 mg/kg/dose of base, maximum of 500 mg) was dissolved in 10 mL of water and infused over 1 to 2 minutes. On day 1 of the study, the nasoenteric tube was inserted into the stomach. By day 3 of the study the tube had passed into the proximal small intestine (SI) just distal to the ligament of Treitz (confirmed fluoroscopically). The balloon was then inflated, and peristalsis propelled the tube distally. Tube position within the cecum was confirmed fluoroscopically on day 5 (day 7 in 4 patients because of slow transit). If the tube had migrated too far, it was retracted into the desired location.

Serum Gastrin, Cysteamine and Leukocyte Cystine Measurements.

After an overnight fast (except for water) blood samples were taken at baseline and at varying intervals after intraluminal delivery of cysteamine. Serum gastrin levels were then measured at 30, 60, 90, and 120 minutes and 3 and 4 hours; cysteamine levels were measured at 0, 5, 10, 20, 30, 45, 60, 75, 90, 105, 120, and 150 minutes and 3, 4, 6, 8, 10, 12, and 16 hours; leukocyte cystine levels were measured at 1, 2, 3, 4, 6, and 12 hours in patients with cystinosis only. Gastrin was measured in picograms/mL with the Diagnostic Products Corporation (Los Angeles, Calif.) gastrin radioimmunoassay-assay kit. Leukocyte cystine levels were measured in nmol half-cystine per mg protein by the Cystine Determination Lab (La Jolla, Calif.).

To measure plasma cysteamine, 100-µL plasma samples were collected in heparinized vacutainers and spun in a centrifuge within 1 hour, and plasma was stored at −18° C. The concentration of cysteamine was measured by use of tandem mass spectroscopy (API 2000 LC/MS/MS; Applied Biosystems, Foster City, Calif.). Cysteamine concentrations were calculated with a calibration curve that was prepared by spiking plasma with buffered cysteamine solutions, and quality control samples were analyzed with each batch.

Statistical Analysis.

Mixed model restricted maximum likelihood (REML) repeated measures analysis of variance with subjects as a random effect was performed on the absolute leukocyte cystine levels, on the leukocyte cystine level changes from baseline, and on the "area over the curve" (AOC) for leukocyte cystine level changes from baseline after cysteamine administration for the subjects with cystinosis. AOC is computationally analogous to area under the curve, but it is applied when values are predominantly decreasing below baseline values. Large AOC values reflect large decreases, and a negative AOC reflects a net increase in value. Main effects for site of delivery, time after delivery, and the interaction between site and time were tested, except just the site effect was tested for AOCs. In the absence of significant interaction when a main effect was detected, Tukey's honestly significant difference test (HSD) was applied to identify where differences occurred within a 5% family wise error rate. The Tukey HSD procedure controls for overall significance level when performing all pairwise comparisons. An additional analysis was performed with plasma cysteamine $C_{max}$ added to the AOC model.

REML repeated measures analyses of variance with subjects as a random effect were also performed as described above on AUC and the $C_{max}$ over time for plasma cysteamine levels separately for the subjects with cystinosis and control subjects and with both subject groups combined. Differences between means for the 3 sites were tested, plus group and group x site interaction effects for the combined groups. If a site effect was detected, Tukey's HSD was applied to determine which sites differed from each other.

REML repeated measures analyses of variance were also performed as described above on gastrin levels. The analyses were performed on 2 versions of datasets: the full dataset and all data after omitting observations collected at 30 minutes (1 subject was missing a blood sample taken at 30 minutes after small intestinal cysteamine delivery). A 5% significance level was used without adjustment for all statistical testing.

Figure 1B:

Six patients with cystinosis, (3 male, 3 female) with a mean age of 15.2 years (range 13-19 years) were recruited into the study (Table I). Eight healthy adult control patients (6 male, 2 female) with a mean age of 23.2 years (range 19-28 years) were enrolled. None of the children with cystinosis had undergone kidney transplantation. All control subjects received 500 mg cysteamine base, whereas the mean dose for subjects with cystinosis was 453 mg (range 406-500 mg). All subjects had normal liver function test results. In all subjects the nasoenteric tube passed successfully from the stomach into the upper SI; however, it did not progress any further in 2 subjects with cystinosis. In 2 of the control subjects the tube only reached the mid-ileum but did, however, progress to the cecum in 8 subjects (4 control subjects, 4 with cystinosis). There were no reported adverse effects with the insertion or removal of the nasoenteric tube (FIG. 1).

Symptoms.

Only 2 patients (1 male, 1 female) with cystinosis reported regular GI symptoms before the study, and these had responded to acid-suppression therapy. The male subject had severe retching and emesis about 15 minutes after receiving intragastric cysteamine but did not have any symptoms when the drug was infused into the proximal small intestine. The female child with cystinosis had mild transient nausea after SI drug delivery only. No other symptoms were reported after any other cysteamine delivery in the children with cystinosis. There were no associated adverse events with tube placement or removal.

Plasma Cysteamine.

Among the subjects with cystinosis as measured by analysis of variance, the mean plasma cysteamine $C_{max}$ and AUCs (of the concentration-time gradient) differed by site of cysteamine delivery (both P<0.03). Site (†) refers to either patients with cystinosis or control subjects. For the plasma cysteamine AUCs, the means differed between the duodenal and both gastric and cecal sites of delivery (Tukey HSD global P<0.05). Among control subjects, the mean AUC did not differ among delivery sites (P>0.4), but mean $C_{max}$ did (P<0.05). For both cystinosis and control groups the mean $C_{max}$ values differed only between the duodenum and cecum; mean $C_{max}$ values after duodenal versus gastric or gastric versus cecal delivery were not statistically different (Tables II and III).

TABLE II

Mean plasma cysteamine $C_{max}$ levels (γmol/L) and area under curve (AUC) measurements in cystinosis subjects, controls, and combined cystinosis and control subjects, after delivery of cysteamine into the stomach, small intestine, and cecum

|  | $C_{max}$ Cystinosis | AUC Cystinosis | $C_{max}$ Control | AUC Control | $C_{max}$ Combined | AUC Combined |
|---|---|---|---|---|---|---|
| Stomach | 35.5 (20.5) | 3006 (1112) | 39.5 (16.4) | 3613 (1384) | 37.8 (17.6) | 3353 (1267) |
| Small Intestine | 55.8 (13.0) | 4299 (1056) | 51.1 (20.7) | 3988 (1659) | 53.2 (17.4) | 4047 (1376) |
| Cecum | 21.9 (13.1) | 3002 (909) | 23.1 (15.3) | 2804 (1323) | 22.5 (13.2) | 2903 (1056) |

The standard deviations are in parenthesis

TABLE III

Comparisons of mean plasma cysteamine $C_{max}$ (γmol/L) and AUC measurements for combined cystinosis subjects and control subjects among delivery sites

|  | AUC | $C_{max}$ |
|---|---|---|
| P value* | <0.01 | <0.01 |
| Stomach vs SI | + | + |
| Stomach vs Cecum | − | − |
| SI vs Cecum | + | + |

Figure 2:
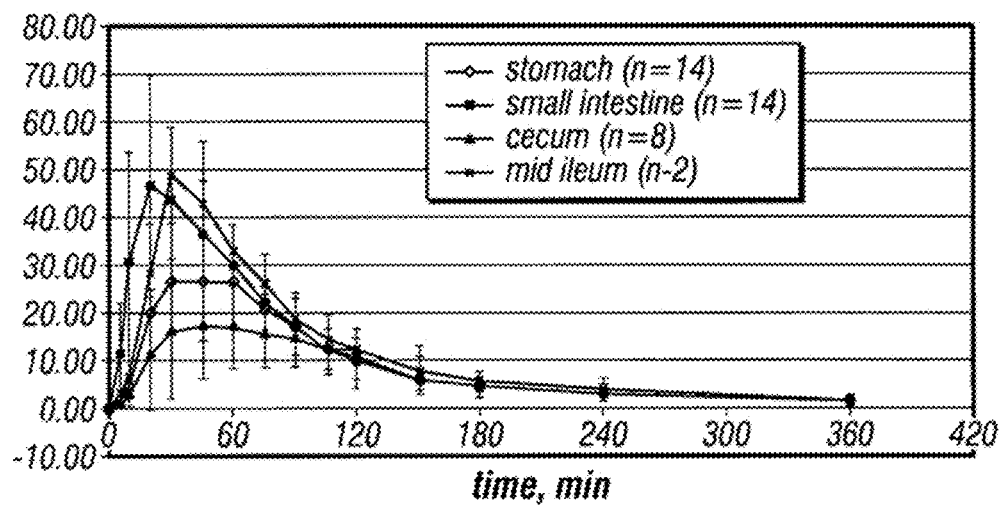
FIG. 2 shows mean plasma cysteamine levels taken from patients with cystinosis and control subjects after delivery of drug into various intestinal sites. Error bars are standard error of the mean. In 2 control subjects, most distal point of drug delivery was the mid-ileal region.

+ Significant difference using Tukey's HSD test (α = 0.05)
− No significant difference
*ANOVA test for equality of three delivery sites When data from the control subjects were combined with cystinosis subject data, there was both a group effect (P<0.05) and a site effect (P<0.01) for AUCs, with a significant difference between mean AUC levels for the duodenum versus both the stomach and cecum. $C_{max}$ values differed among sites (P<0.01) but not between groups (P>0.4). Group (*) refers to site of intestinal delivery. $C_{max}$ differed between duodenum versus both stomach and cecum (FIG. 2).

Leukocyte Cystine.

Figure 3:
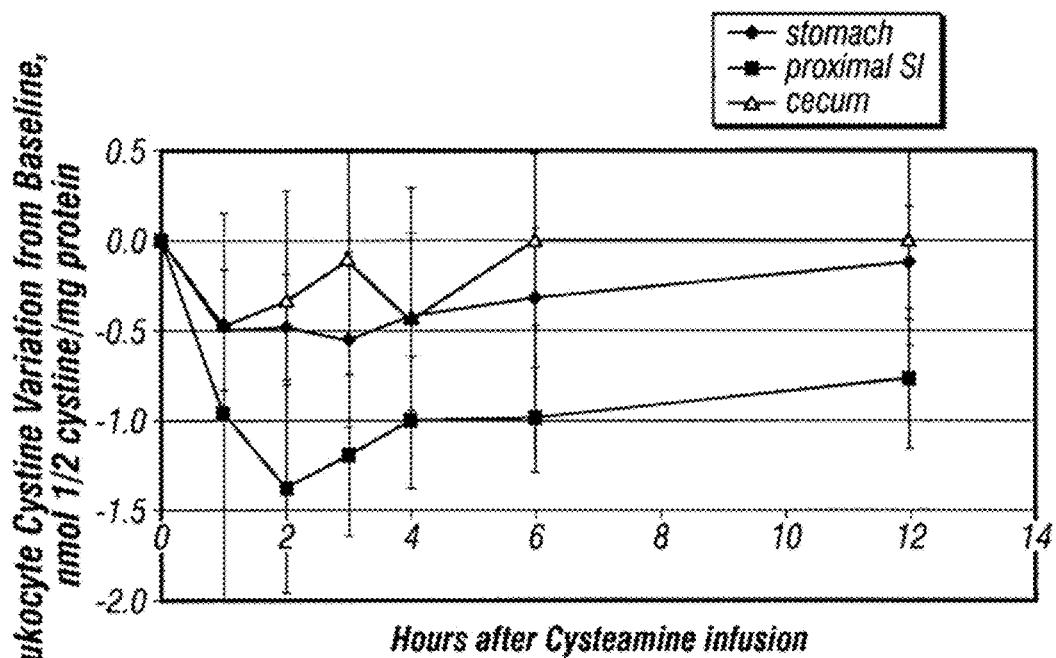
FIG. 3 shows the mean change in leukocyte cystine levels, compared with baseline levels, over a 12-hour period following delivery of cysteamine into varying intestinal sites. Negative levels signify increased leukocyte cystine depletion compared with baseline.
Figure 4:
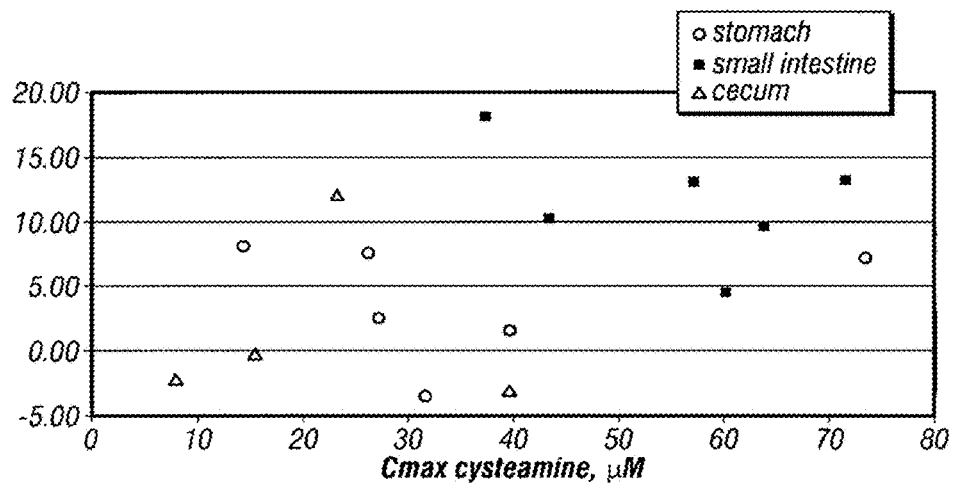
FIG. 4 shows a scatterplot of plasma cysteamine $C_{max}$ vs. AOC of WBC Cystine changes from Baseline. Positive value means decrease from baseline. Negative value means increase from baseline. AOC change from baseline was affected by $C_{max}$ for cysteamine (P<0.001).

There were significant differences among the 3 sites of delivery for cystine levels (P<0.04), changes from baseline values (P<0.0001), and AOCs for changes from baseline (P<0.02). A Tukey HSD test, which controls for multiple comparisons, showed that mean leukocyte cystine levels differed between the cecum and stomach sites, but that cecum versus duodenum and stomach versus duodenum produced similar mean values. When the absolute cystine levels or AOCs for changes from baseline levels were evaluated, the significant differences in sites were found between the duodenum and both the stomach and cecum, but not between stomach and cecum (Tukey HSD global P<0.05) (FIG. 3). Plasma cysteamine $C_{max}$ and AUC con-tributed a statistical effect on AOC (P<0.001 and <0.02, respectively), even after controlling for delivery site (FIG. 4).

Blood Gastrin.

For the full gastrin dataset, there was a significant difference among the means for the different delivery sites (P<0.1), with the cecum resulting in a lower mean from that of the stomach and small intestine. Both group * and site † significant effects were detected after omitting observations from 30 minutes after delivery (P<0.05 and P<0.01, respectively). The 30-minute observations were omitted because of a missing data set. For these observations, mean levels of gastrin after delivery in the cecum were different from those from both the duodenum and stomach, although the latter did not differ from each other. The 1 boy (14 years) who had severe GI symptoms after intragastric, but not enteric or cecal, cysteamine delivery had a rise in baseline gastrin from 70 pg/mL to 121 pg/mL at 30 minutes after gastric cysteamine. Within the control group, more than half of the baseline and post-cysteamine gastrin levels remained undetectable (<25 pg/mL), and none of the control subjects had a significant rise in gastrin after cysteamine delivery into any site.

Patients with cystinosis are required to ingest oral cysteamine (Cystagon®) every 6 hours, day and night. When taken regularly, cysteamine can deplete intracellular cystine by up to 90% (as measured in circulating white blood cells), and this has been shown to reduce the rate of progression to kidney failure/transplantation and also to obviate the need for thyroid replacement therapy. Unfortunately, because of the strict treatment regimen and the associated symptoms, non-adherence with cysteamine therapy remains a problem, particularly among adolescent and young adult patients. Certainly, by reducing the frequency of required cysteamine dosing adherence can be improved. The disclosure shows a strong statistical association between the maximum plasma concentration ($C_{max}$) of cysteamine and AOC measurements for leukocyte cystine (P<0.001). A higher $C_{max}$ is achieved after delivery of cysteamine into the small intestine than when infused into the stomach or colon; this may be due to improved absorption rate from the SI, greater surface area of the SI, or less cysteamine undergoing hepatic first pass elimination when absorbed rapidly through the small intestine. When data were combined for patients with cystinosis and control subjects, there was a statistical difference between duodenal versus both gastric and colonic delivery for plasma cysteamine $C_{max}$ and AUC levels (both P<0.05). The lack of similar statistical significance for the cystinosis group alone may simply reflect the small number of patients studied. Changes from baseline leukocyte cystine levels were statistically significant for absolute cystine levels and for AOC when cysteamine was infused into the duodenum compared with both stomach and colon. As shown in FIG. 3, the leukocyte cystine levels remained below pre-delivery levels for up to 12 hours after a single dose of cysteamine into the small intestine. This would suggest that effective absorption of cysteamine through the SI, by causing a higher $C_{max}$ and AUC on the cysteamine concentration-time gradient, could lead to prolonged depletion of leukocyte cystine and possibly less frequent daily dosing. Another explanation would be that by achieving a high enough plasma cysteamine concentration, more drug reaches the lysosome (where cystine accumulates). In the lysosome the cysteamine reacts with cystine forming the mixed disulfide of cysteamine and cysteine. The mixed disulfide exits the lysosome presumably via the lysine carrier. In the cytosol the mixed disulfide can be reduced by its reaction with glutathione. The cysteine released can be used for protein or glutathione synthesis. The cysteamine released from the mixed disulfide reenters the lysosome where it can react with another cystine molecule. Thus 1 molecule of cysteamine may release many molecules of cystine from the lysosome. This study showed a dramatic decrease in leukocyte cystine within an hour of cysteamine delivery. In retrospect, the finding from this study was that the leukocyte cystine levels remained at the 1-hour level for 24 hours, and even at 48 hours after delivery the levels had not returned to the pre-cysteamine level.

Cysteamine is a potent gastric acid-secretagogue that has been used in laboratory animals to induce duodenal ulceration; studies in humans and animals have shown that cysteamine-induced gastric acid hypersecretion is most likely mediated through hypergastrinemia. In previous studies performed in children with cystinosis who suffered regular upper gastrointestinal symptoms, a single oral dose of cysteamine (11-23 mg/kg) was shown to cause hypergastrinemia and a 2- to 3-fold rise in gastric acid-hypersecretion. Symptoms suffered by these individuals included abdominal pain, heartburn, nausea, vomiting, and anorexia. Interestingly, only 2 of 6 subjects with cystinosis (who were known to suffer regular cysteamine-induced GI symptoms) had increased gastrin levels and symptoms, including nausea, retching, and discomfort after intragastric cysteamine. Gastrin levels were only available after small intestinal administration in 1 of the 2 children and the levels remained the same as baseline. Neither child had symptoms after enteric cysteamine delivery. None of the other patients with cystinosis or control subjects had an increase in gastrin levels with cysteamine infused into any site. This would suggest that cysteamine-induced hypergastrinemia may arise as a local effect on the gastric antral-predominant G-cells only in susceptible individuals. In addition, plasma gastrin levels usually peaks after intragastric delivery within 30 minutes, whereas the plasma cysteamine levels peaked later.8,10 In 2 previous studies, children with cystinosis were shown to have a significant rise in plasma gastrin levels after receiving intragastric cysteamine; as part of these study's entry criteria all subjects did, however, suffer with regular GI symptoms. Data from this study would suggest that cysteamine does not cause hypergastrinemia, and therefore acid-hypersecretion, in all patients with cystinosis. Thus acid suppression therapy would not be recommended in patients with cystinosis without upper GI symptoms.

The data suggest that direct administration of cysteamine into the jejunum may result in prolonged leukocyte cystine depletion. In a previous study, a child who had a gastrojejunal feeding tube for oral feeding aversion and severe UGI symptoms, responded to intrajejunal cysteamine with a 3-fold rise in serum gastrin as compared with drug administration into the stomach. The leukocyte cystine response was not measured in this child. Therefore patients with jejunal feeding tubes will have to be further evaluated.

Figure 5:
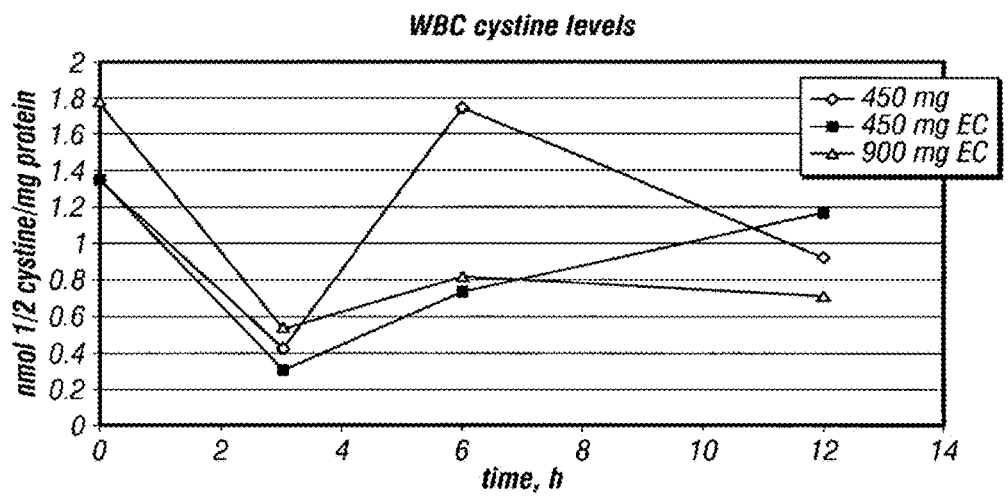
FIG. 5 shows serial leukocyte cystine levels after drug was given as normal Cystagon® and enteric-coated (EC) cysteamine on alternate days. These serial levels were taken during the inpatient phase of the study. Desired cystine levels are below 1 mmol 1/2cystine/mg protein. Higher dose enteric-coated (yellow)) drug resulted in prolonged cystine suppression with 12 hour levels still within desired range.
Figure 6:
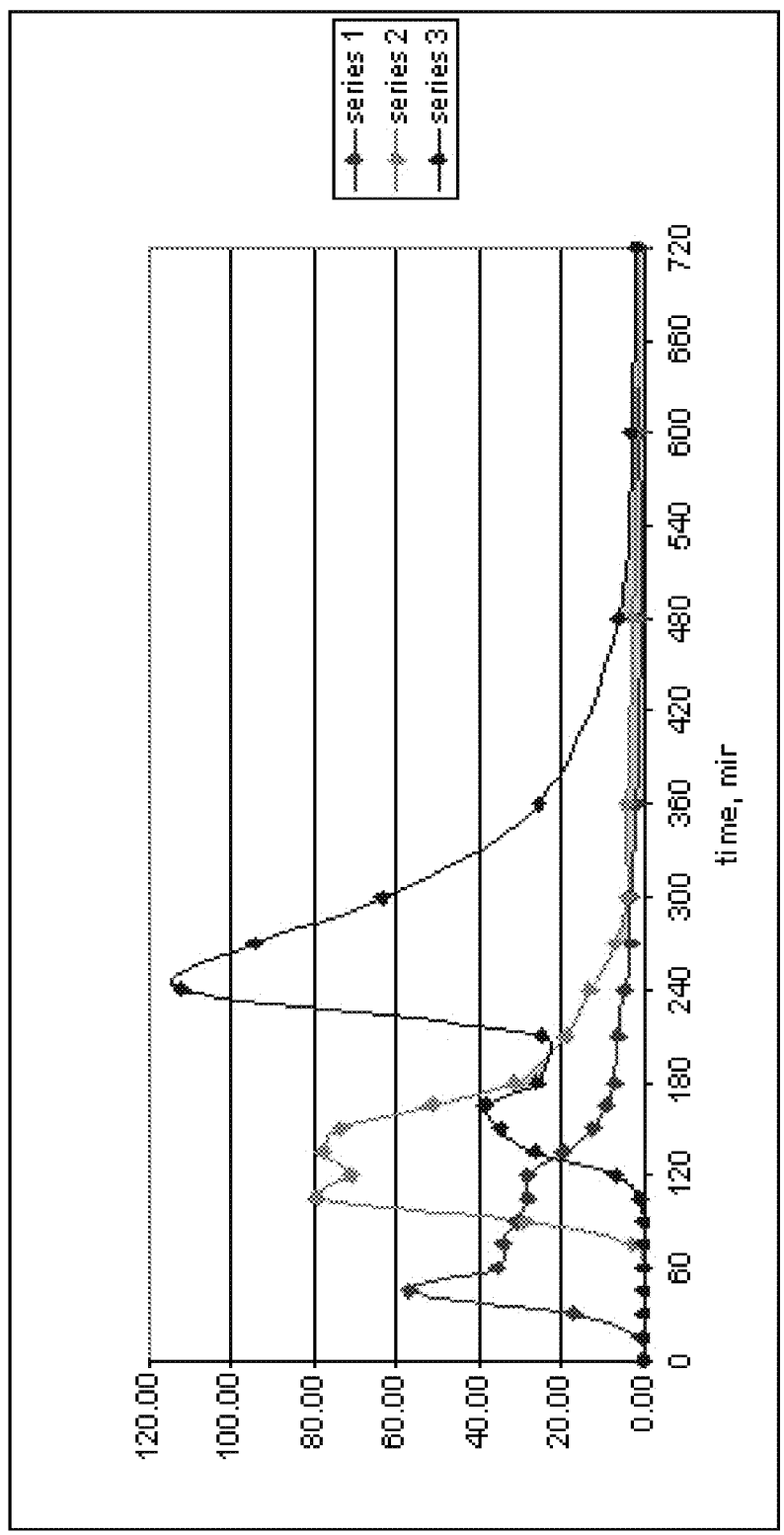
FIG. 6 shows the blood cysteamine levels following a single 450 mg dose of Cystagon® (series 1), 450 mg EC-cysteamine (series 2) and 900 mg EC-cysteamine (series 3). The $C_{max}$ is higher following EC drug. In addition, the time to $C_{max}$ is longer following EC-drug, suggesting that the drug is released from the capsule within the small intestine rather than the stomach.

FIGS. 5 and 6 shows results from a patient that remained on the twice daily EC-cysteamine for an extended period of time. Over this period the patient's leukocyte cystine levels have been measured regularly. The dose of twice daily EC-cysteamine is titrated against the patient's symptoms and cystine levels. The patient's cystine levels have been 0.4, 1.0, 0.36.

This study provides data that may be used to improve the quality of life for patients with cystinosis. The present formulation of Cystagon® comprises cysteamine in a capsule that will dissolve rapidly on contact with water, most likely within the stomach.

Although a number of embodiments and features have been described above, it will be understood by those skilled in the art that modifications and variations of the described embodiments and features may be made without departing from the teachings of the disclosure or the scope of the invention as defined by the appended claims.

What is claimed is:

1. A method of treating nephropathic cystinosis in a subject, comprising administering to said subject a composition comprising an effective amount of an enterically coated pharmaceutically acceptable prodrug of cysteamine.

2. The method of claim 1, wherein the enteric coating releases the cysteamine, or a pharmaceutically acceptable salt thereof, at a pH of 4.5 or greater.

3. The method of claim 1, wherein the frequency of administering is less than four times daily.

4. The method of claim 3, wherein the frequency of administering is twice per day.

5. The method of claim 2, wherein the cysteamine salt is cysteamine bitartrate.

6. The method of claim 5, wherein each administration comprises an amount of cysteamine bitartrate that would yield a dose of 100 to 1000 mg cysteamine free base.

7. The method of claim 1, wherein the composition is orally administered.

8. The method of claim 1, wherein the total daily dose of cysteamine is about 1.35 $g/m^2$/day.

9. The method of claim 1, wherein the composition is in the form of a capsule.

10. The method of claim 1, wherein the composition is in the form of a tablet.

* * * * *